(12) United States Patent
Grubbs et al.

(10) Patent No.: US 11,844,724 B2
(45) Date of Patent: *Dec. 19, 2023

(54) METHOD FOR EYE LENS REMOVAL USING CAVITATING MICROBUBBLES

(71) Applicants: California Institute of Technology, Pasadena, CA (US); The Regents of the University of California, Oakland, CA (US); United States Government represented by the Department of Veterans Affairs, Washington, DC (US)

(72) Inventors: Robert H. Grubbs, South Pasadena, CA (US); Marshall L Stoller, San Francisco, CA (US); Ying Han, Burlingame, CA (US); Frank L. Brodie, Durham, NC (US)

(73) Assignees: California Institute of Technology, Pasadena, CA (US); The Regents of the University of California, Oakland, CA (US); United States Government represented by the Department of Veterans Affairs, Washington, DC (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/509,641

(22) Filed: Oct. 25, 2021

(65) Prior Publication Data
US 2022/0040000 A1  Feb. 10, 2022

Related U.S. Application Data

(63) Continuation of application No. 16/733,918, filed on Jan. 3, 2020, now Pat. No. 11,166,846.
(Continued)

(51) Int. Cl.
*A61F 9/007* (2006.01)

(52) U.S. Cl.
CPC ................ *A61F 9/00745* (2013.01)

(58) Field of Classification Search
CPC ... A61M 37/0092; A61M 31/00; A61K 41/13; A61K 49/223; A61K 38/00; A61B 8/10;
(Continued)

(56) References Cited

U.S. PATENT DOCUMENTS

| 4,135,516 A | 1/1979 | Spina et al. |
| 4,642,116 A | 2/1987 | Clayman et al. |

(Continued)

FOREIGN PATENT DOCUMENTS

| WO | 2009033107 A2 | 3/2009 |
| WO | 2013028942 A1 | 2/2013 |

OTHER PUBLICATIONS

Dular et al., "High Speed Observation of Damage Created by a Collapse of a Single Cavitation Bubble", Wear, vols. 418-419, Jan. 15, 2019, pp. 13-23.
(Continued)

*Primary Examiner* — Timothy J Neal
*Assistant Examiner* — Andrew P. Restaino
(74) *Attorney, Agent, or Firm* — Mark P. Mathison

(57) ABSTRACT

A surgical method of cataract fragmentation and extraction via microbubble cavitation is described. In particular, gas-filled microbubbles are injected into a lens capsule of a subject's eye, and cavitation of the microbubbles is activated by applied ultrasound energy. The ultrasound energy can be applied from an external device. The cavitation fragments cataract tissues without damaging other tissue, such as the lens capsule. Fragmented lens material is then aspirated from the lens capsule. The method can be used alone or in conjunction with other methods, such as phacoemulsification.

20 Claims, 11 Drawing Sheets

Related U.S. Application Data

(60) Provisional application No. 62/788,452, filed on Jan. 4, 2019.

(58) Field of Classification Search
CPC ....... A61B 8/481; A61B 8/483; A61B 3/1233; A61B 8/06; A61B 8/12; A61B 8/13; A61B 8/4488; A61B 8/08; A61N 7/00; A61F 9/008; A61F 2009/00863; A61F 9/00745; G01N 2203/0076; G01N 2203/0658
See application file for complete search history.

(56) References Cited

U.S. PATENT DOCUMENTS

| | | | |
|---|---|---|---|
| 5,213,569 | A | 5/1993 | Davis |
| 7,316,664 | B2 * | 1/2008 | Kadziauskas ......... B06B 1/0253 604/44 |
| 8,658,205 | B2 | 2/2014 | Hui et al. |
| 10,149,906 | B2 | 12/2018 | Grubbs et al. |
| 10,220,104 | B2 | 3/2019 | Robinson et al. |
| 10,357,565 | B2 | 7/2019 | Grubbs et al. |
| 11,166,846 | B2 | 11/2021 | Grubbs et al. |
| 2008/0014627 | A1 * | 1/2008 | Merchant .......... A61M 37/0092 435/259 |
| 2009/0149840 | A1 | 6/2009 | Kurtz |
| 2013/0261535 | A1 | 10/2013 | Behar-Cohen |
| 2015/0359666 | A1 | 12/2015 | Zacharias |
| 2016/0346121 | A1 | 12/2016 | Ianchulev et al. |
| 2018/0021557 | A1 | 1/2018 | Fawzi et al. |
| 2018/0185272 | A1 | 7/2018 | Marx et al. |

OTHER PUBLICATIONS

PCT/US2020/012204, "International Preliminary Report on Patentability", dated Jul. 15, 2021, 7 pages.
PCT/US2020/012204, "International Search Report and Written Opinion", dated Mar. 11, 2020, 9 pages.
EP20736036.3, "Extended European Search Report", dated Jul. 28, 2022, 9 pages.

* cited by examiner

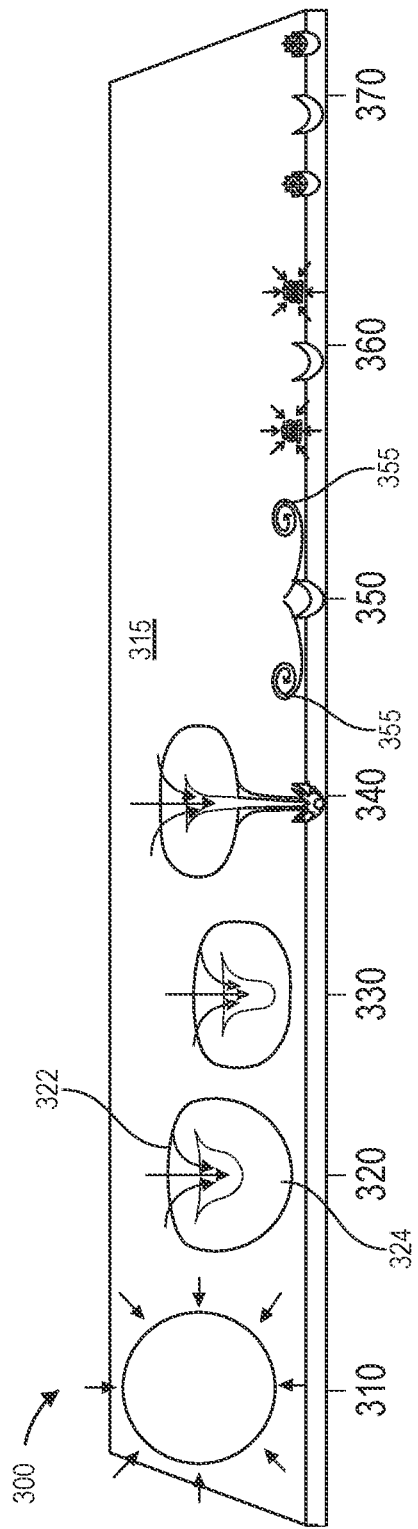

METHOD FOR EYE LENS REMOVAL USING CAVITATING MICROBUBBLES

CROSS-REFERENCES TO RELATED APPLICATIONS

This application is a continuation of U.S. patent application Ser. No. 16/733,918, filed Jan. 3, 2020, which claims the benefit of U.S. Provisional Patent Application No. 62/788,452, filed Jan. 4, 2019, which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under grant no. R21 EY028747 awarded by The National Institutes of Health. The government has certain rights in the invention.

BACKGROUND

1. Field of the Invention

The present application generally relates to cataract extraction surgery. Specifically, it relates to cataract fragmentation and extraction using microbubble cavitation, which may be augmented by ultrasound energy.

2. Description of Related Art

A cataract is the opacification of the natural phakic lens in the eye. Cataracts occur most commonly due to aging, but can also be secondary to congenital defect, trauma, medication, systemic disease or ocular surgery. Cataracts are the leading cause of visual impairment in the United States, and the most common cause of blindness in the developing world. Virtually all people who live long enough eventually require cataract surgery to maintain good vision. Cataract surgery is one of the most commonly performed surgeries in the United States, with over 3.6 million procedures performed in 2015.

Conventional phacoemulsification methods for surgical cataract extraction are effective at fragmenting and emulsifying the lens but have significant safety drawbacks. Possible vision-threatening complications can occur in approximately 1% to 4% of phacoemulsification procedures, for patients who would otherwise have excellent post-operative vision. Accordingly, cataract surgical training is the key and one of the most important components of a 3-year ophthalmic surgery residency. Moreover, even in an uncomplicated surgery with skilled hands, the energy produced by the phacoemulsification process may lead to a loss of corneal endothelial cells. This can lead to prolonged healing times and ultimately to corneal decompensation with irreversible clouding, necessitating corneal surgery.

Besides the human toll of the safety drawbacks, conventional phacoemulsification often requires significant equipment expenditure both in capital expenditure and ongoing costs for the disposable supplies.

Thus, there is a need for another method of cataract extraction capable of augmenting or replacing conventional high-energy phacoemulsification techniques.

BRIEF SUMMARY

A surgical method of cataract fragmentation and extraction via microbubble cavitation is described. In particular, the cavitation of injected microbubbles is activated by ultrasound energy. The cavitation can efficiently fragment cataracts without damaging other tissue, such as the subject's lens capsule. The method can also be used to augment phacoemulsification.

Gas-filled microbeads are applied into a lens capsule holding the cataract. Ultrasound energy is directed at the microbeads, inducing cavitation. The cataractous lens material is fragmented, while the lens capsule is preserved. The fragmented lens material is aspirated from the capsule.

In one aspect of this disclosure, a method for removing a lens from an eye comprises providing gas-filled microbeads having an outside diameter less than 500, 250, or 100 microns. The method further comprises injecting the microbeads into an eye, wherein the eye contains a cataractous lens of a subject. For example, the microbeads may be injected into a lens capsule of the subject holding the cataractous lens. The method further comprises directing ultrasound energy at the injected microbeads sufficient to cause the microbeads to undergo cavitation. The method further comprises fragmenting lens material with the cavitation while preserving the posterior lens capsule. The method further comprises aspirating the fragmented lens clumps from the lens capsule.

In some embodiments, the method further comprises repeating the injecting, directing, fragmenting, and aspirating to remove the entire cataractous lens from the subject.

In some embodiments, each of the microbeads is comprised of a phospholipid shell and a fluorinated alkane gas inside the shell.

In some embodiments, the fluorinated alkane gas is selected from the group consisting of perfluoropropane and butane.

In some embodiments, each of the microbeads is comprised of a multiphase polymer shell and air inside the shell.

In some embodiments, the microbeads are coated with a targeting moiety configured to bind to lens material. The method may further comprise binding the microbeads to lens material of the cataractous lens. In various embodiments, the lens material may be lens fiber protein, or another lens material, and is not limited by the present disclosure.

In some embodiments, the targeting moiety comprises polypeptides or acidic groups.

In some embodiments, the method further comprises performing a capsulorhexis on the anterior lens capsule. The method may further comprise hydrodissecting the cataractous lens from the lens capsule. The method may further comprise inserting an artificial intraocular lens into the lens capsule.

In some embodiments, the microbeads are injected along with hydrodissecting liquid.

In some embodiments, the microbeads are injected into or around the cataractous lens.

In some embodiments, the microbeads are in a liquid suspension, and the injecting includes injecting the liquid suspension into the lens capsule.

In some embodiments, the liquid suspension is used to irrigate the lens capsule.

In some embodiments, the ultrasound energy reaches the microbeads by being transmitted through biological tissue from outside of the lens capsule.

In some embodiments the ultrasound energy originates outside of the eye.

In some embodiments, the ultrasound energy is transmitted from within the lens capsule using an ultrasonic tip.

In some embodiments, the method further comprises inserting a phacoemulsification handpiece tip into the lens capsule. The method may further comprise emulsifying, during or after the fragmenting, the lens material using emulsifying ultrasonic energy transmitted from the phacoemulsification handpiece tip within the lens capsule. Less emulsifying ultrasonic energy from the phacoemulsification handpiece tip inside the lens capsule may be required to remove the cataractous lens than if the fragmenting with the cavitation were not performed.

In some embodiments, the subject is a mammal, such as a human, a dog, or a rabbit.

BRIEF DESCRIPTION OF THE DRAWINGS

FIG. 3 illustrates an example cavitation process, in accordance with an embodiment.

DETAILED DESCRIPTION

The disclosed system and method of cataract fragmentation and extraction improves over conventional phacoemulsification techniques.

Technical advantages of some of the system and method embodiments include improved safety and efficiency of cataract removal surgery, reduced costs associated with phacoemulsification, and lowered training requirements or less of a learning curve for ophthalmological surgical residents.

I. Cataract Surgery and Potential Complications

The goal of cataract surgery is to extract a cataractous lens and implant an artificial lens in its place. The standard modern technique for cataract extraction relies on phacoemulsification (also referred to as "phaco"), or fragmenting the cataract, emulsifying it with irrigating fluid, and aspirating the emulsified cataract from the eye. The basis for fragmenting and emulsifying the cataract is that removing the cataract in pieces, rather than en bloc, permits surgery through a corneal incision significantly smaller than the diameter of the lens. This can minimize ocular trauma and post-operative defects, such as astigmatism.

Figure 1A:
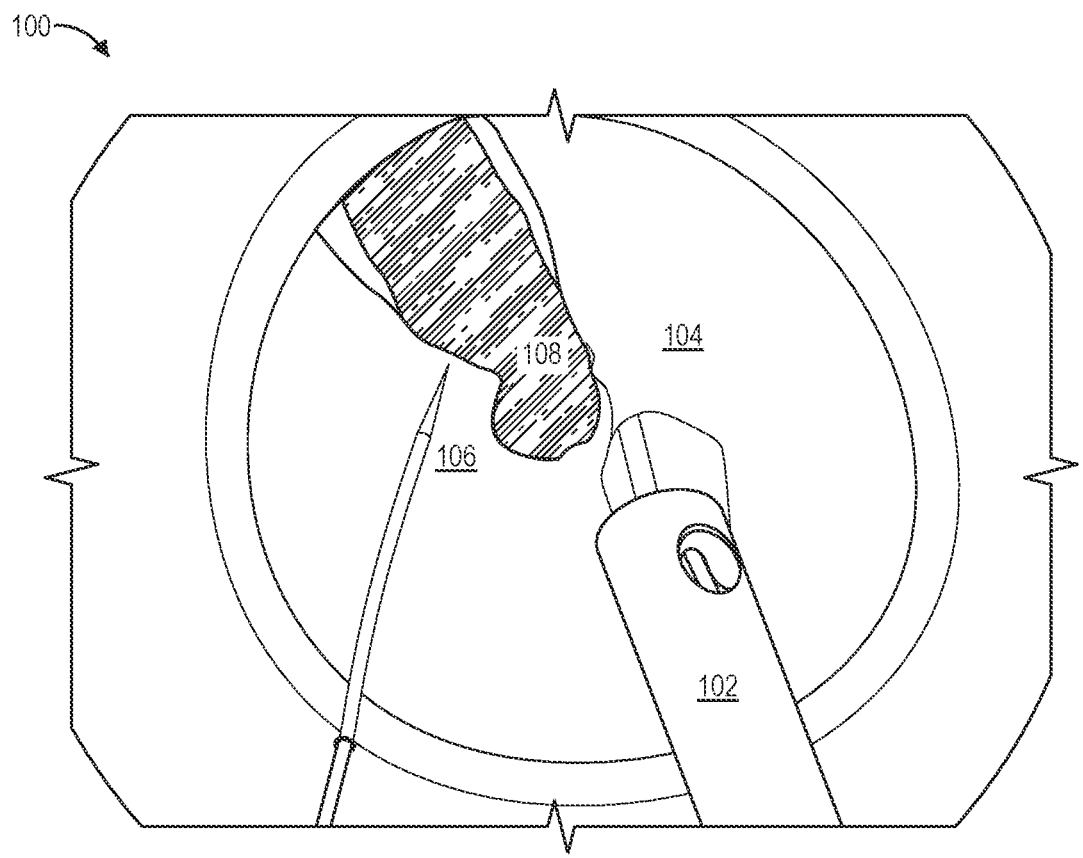
FIG. 1A illustrates an example cataract surgery of the prior art.

FIG. 1A illustrates an example cataract surgery 100 incorporating traditional phacoemulsification of the prior art. The phacoemulsification handpiece 102 is inserted through a corneal incision and the opening in the capsular bag to engage the cataractous lens 104. There, through a combination of pulsed ultrasonic energy emitted by the phacoemulsification handpiece 102 and mechanical separating techniques using a second rigid instrument 106, also referred to as a 'chopper,' lens 104 is fragmented and emulsified to the point it can be aspirated through the small opening of the phacoemulsification handpiece 102. In this example, lens 104 is already partially fragmented, and has a missing fragment 108.

In standard phacoemulsification techniques for cataract extraction, a surgeon or nurse dilates the patient's pupil. Next, the surgeon makes an incision at the limbus of the cornea and performs capsulorhexis, or incises a small opening in the surface of the capsular bag (also referred to as the lens capsule), a thin membrane housing phakic lens 104. Frequently the surgeon will then inject liquid between the lens and capsule to separate, or hydrodissect, them apart. The surgeon then uses the phaco handpiece 102 to perform ultrasonic phacoemulsification, that is, to deliver ultrasonic waves that fragment the cataractous lens 104. The handpiece also aspirates and removes the emulsified cataractous lens 104 from the eye while irrigating, to maintain a stable volume of fluid in the eye. The surgeon then deposits an artificial intraocular lens into the capsular bag.

Figure 1B:
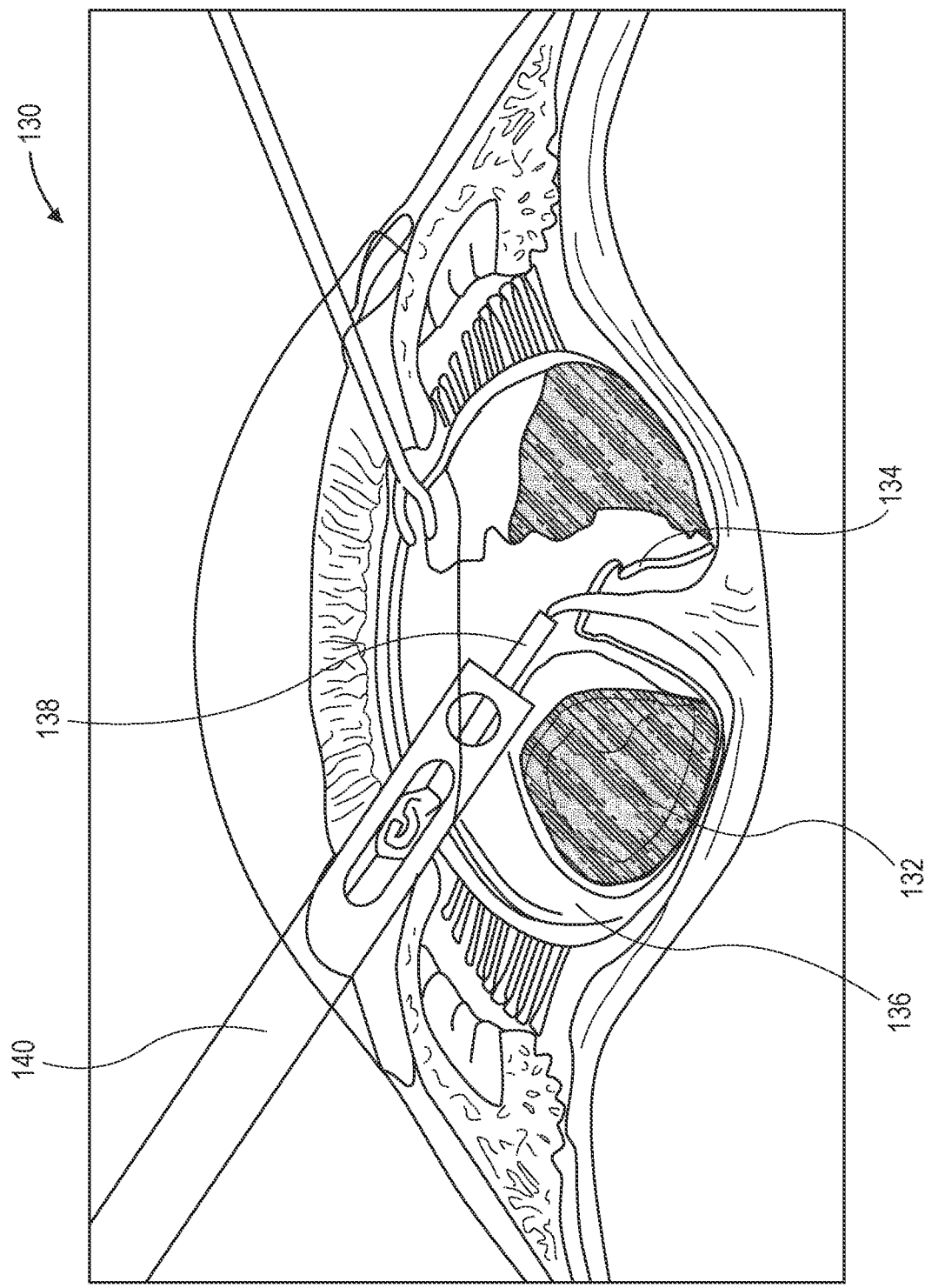
FIG. 1B illustrates potential complications in an example cataract surgery of the prior art.

FIG. 1B illustrates a potential complication in an example cataract surgery 130 of the prior art. Although the phacoemulsification method for cataract extraction is very effective for fragmenting and emulsifying the lens 132, it has considerable safety drawbacks. One common complication, capsular bag rupture 134, can permanently damage a structure within the eye. Learning to avoid capsular bag rupture necessitates extensive surgical training before ophthalmological surgeons are qualified to perform cataract removal.

The human eye's phakic, or natural, lens 132 is situated within a very thin (tapering from approximately 5 μm to 15 μm) membrane posterior to the iris called the capsular bag 136 (also referred to as the lens capsule), and is supported for 360 degrees with zonular fibers. Rupture of the capsular bag can occur when the sharp needle tip 138 of phaco handpiece 140 breaks the capsular bag 136. Because needle tip 138 moves quickly during surgery, and fluids such as the irrigation fluid may be flowing rapidly, it is challenging for a surgeon to avoid inadvertently contacting capsular bag 136 with needle tip 138. Moreover, during aspiration of the emulsified cataract, membrane 136 can be drawn toward tip 138, increasing the risk of inadvertent contact. Thus, capsular bag rupture 134 can happen very quickly and abruptly if the surgeon accidentally contacts or aspirates the capsular bag 136, with little opportunity to correct such an error. This can result in a large hole 134 in capsular bag 136, which may immediately become unusable once damaged.

Phacoemulsification can also lead to other serious complications. For example, the sharp tip 138 of phaco handpiece 140 can also inadvertently damage many other delicate and critical structures in the eye, including the cornea and iris. Its ultrasound energy may cause wound burns, as described further below.

Figure 1C:
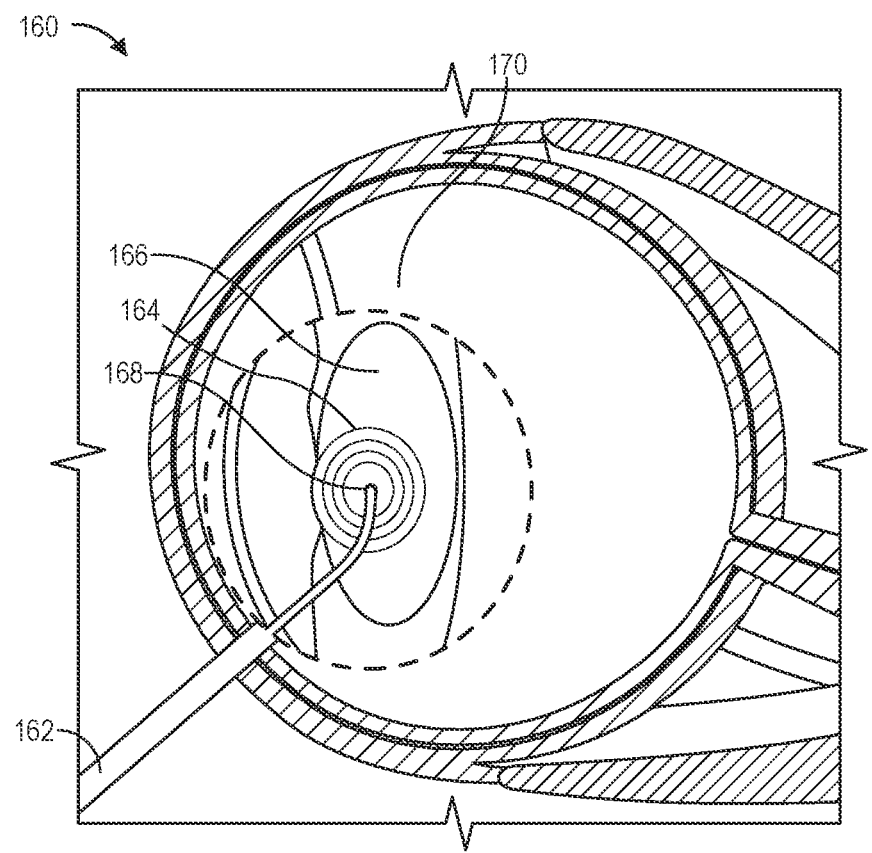
FIG. 1C illustrates aspects of conventional, prior art phacoemulsification procedures that have the potential to cause complications, damage, or discomfort.

FIG. 1C illustrates aspects 160 of conventional, prior art phacoemulsification procedures that have the potential to cause complications, damage, or discomfort. As described in the example of FIG. 1B above, capsular bag rupture is a somewhat common and serious complication. However, there are a number of other complications, sources of discomfort, or impracticalities that sometimes arise in conventional phacoemulsification. Some complications may be mild (requiring medication), while others may require additional surgery and/or engender long term inflammation, retinal detachment, infection, or permanent vision loss or blindness. Studies suggest the total complication rate for phacoemulsification is approximately 1-4%. In this example, the contributing factors or potential sources of such complications, discomfort, and impracticalities are described.

First, the phacoemulsification handpiece 162 combines several functions, including emitting ultrasound energy 164 to fragment cataract 166, mechanically cutting the cataract 166, and aspirating the emulsified cataract. Thus, phaco handpiece 162 is a relatively large instrument, requiring a corneal limbal incision 168 of over 2 mm. In fact, the size of phaco handpiece 162 is often the limiting factor in the required corneal incision size during cataract surgery. Such a corneal incision poses dangers of eye trauma or wound leak.

Within eye 170, the phacoemulsification handpiece 162 requires a sharp metal tip to insert into the cataractous lens and effectively deliver the pulsed ultrasonic energy 164. During the course of surgery, this sharp tip can inadvertently damage many of the delicate and critical structures in the eye, including the cornea, iris, and the lens capsule, as described in the example of FIG. 1B above. Note that phacoemulsification is a mature technique that has already been optimized extensively, yet previous techniques have failed to make the needle tip smaller and safer. Furthermore, the manipulation of the lens 166 required in phacoemulsification can stress and tear the lens capsule and zonules.

In addition, because ultrasound energy 164 is poorly targeted to lens 168, the dose of ultrasound energy 164 delivered into eye 170 may be substantially larger than the mechanical energy needed to fragment cataract 168. Such a large dose potentially causes complications and side effects 160. For example, if there is any disruption to the cooling irrigation mechanism of the phacoemulsification handpiece 162 while producing the large dose of ultrasound energy 164, handpiece 162 can produce damaging wound burns in the surrounding tissue near the insertion site of probe 162. These burns may frequently lead to reoperation, infection, and potentially blinding complications. The disclosed system and methods can lower the risk of such burns, both by reducing the ultrasound dose, and, in some embodiments, by generating the ultrasound outside of eye 170.

Likewise, the dispersion and reflection of poorly-targeted ultrasound waves 164 delivers significant energy to tissues of eye 170 away from the desired target, cataract 166, thereby potentially damaging vital structures or tissues. Even in uncomplicated surgery, the ultrasound energy 164 in phacoemulsification has been shown to lead to damage and loss of corneal endothelial cells in a dose-related fashion. The loss of these corneal endothelial cells can lead to prolonged healing times and ultimately corneal decompensation with irreversible clouding. This may necessitate additional corneal surgery. Beyond surgical complications, phacoemulsification also faces several practical issues: for example, the need to sterilize all the instruments involved in the procedure and the need to replace disposable phaco "packs" after each procedure.

Likewise, phacoemulsification carries significant equipment expenses. For example, disposable supplies such as the phaco "packs" may cost $100 to $200 per procedure, and capital expenditure such as a phaco machine may cost $50,000 to $100,000.

Because complications 160, including possibly vision-threatening ones, can occur in patients who would otherwise have excellent post-operative vision, cataract surgical training is currently the key and one of the most important components during the 3-year ophthalmic surgery residency. Thus, by simplifying current surgical procedures and techniques, the disclosed system and methods can both benefit patients and also improve ophthalmology training.

II. Cavitation of Microbubbles

An alternative or complementary method for cataract fragmentation and extraction is disclosed herein. The disclosed system fragments the cataract primarily by means of microbubble cavitation. Cavitation is the process by which a microbubble expands and collapses, with a resultant micro jet causing damage to surrounding matter. It is known well for surface pitting in metal marine propellers. In some embodiments, the energy required for the expansion is provided by ultrasound radiation.

Generally, microbubbles may form spontaneously, and may subsequently undergo cavitation spontaneously, in areas of rapid flow change (e.g., the phaco needle tip, propellers, pipe areas of changing diameter). However, the disclosed system and methods may instead make use of chemically or physically stabilized microbubbles. Moreover, these stabilized microbubbles can be activated by external energy sources providing sufficient activation energy, and once active, can undergo cavitation at a controlled rate. For example, the microbubbles can be activated by low-energy ultrasound waves or electromagnetic radiation, which can be applied either ab interno or ab externo.

Figure 2A:
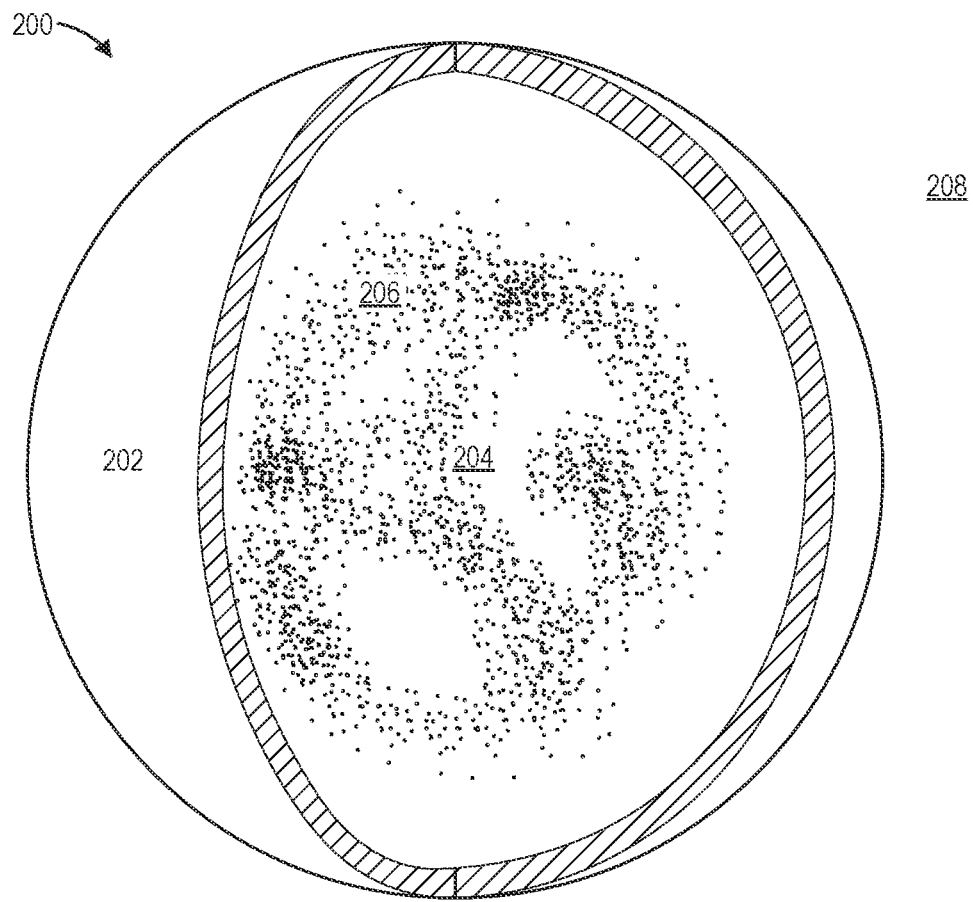
FIG. 2A illustrates an example microbubble, in accordance with embodiments.

FIG. 2A illustrates an example microbubble 200, in accordance with embodiments. Microbubble 200 may include an outer shell 202 and an interior core 204. Interior core 204 may contain gas 206 or liquid with a lower boiling-point from the surrounding aqueous environment 208. Shell 202 may protect interior core 204 from the aqueous environment 208.

In some embodiments, the microbubble 200 used may be a DEFINITY® microbead produced by Lantheus Medical Imaging, Inc. of North Billerica, MA, USA. U.S. Pat. No. 8,658,205 to Hui et al. and U.S. Pat. No. 10,220,104 to Robinson et al. describe such microbubbles and uses for cardiac imaging. Note that the DEFINITY® microbeads may be used with moderately higher-energy ultrasound than would be used for a contrast agent in cardiac imaging applications, but still significantly lower-energy ultrasound than in conventional phacoemulsification. In some embodiments, the microbubbles may be created or modified to target particular matter. U.S. Pat. Nos. 10,149,906 and 10,357,565 to Grubbs et al. describe modifications for biological targets. In some embodiments, other microbubbles may be used, and are not limited by the present disclosure.

Moreover, in some embodiments, the system may include a related apparatus or system used for mixing or agitating a precursor substance in order to form the microbubbles, such as the VIALMIX® activation device for use with DEFINITY® microbeads, also produced by Lantheus Medical Imaging, Inc. In some embodiments, the system may include a related microbubble apparatus.

Figure 2B:
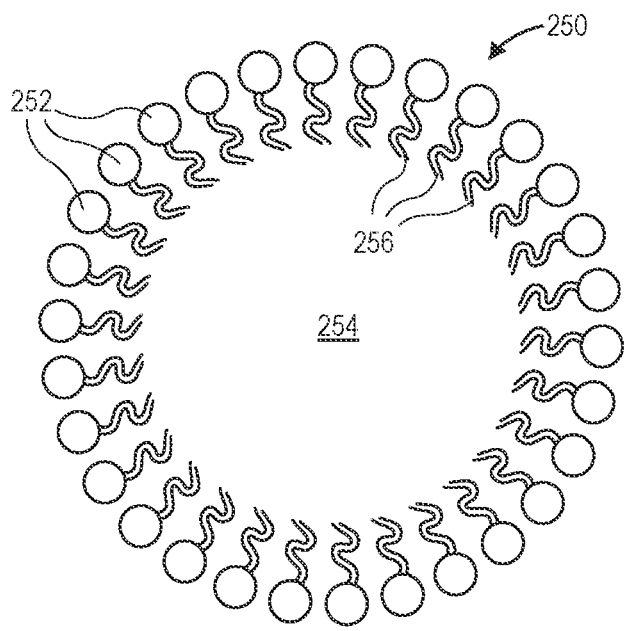
FIG. 2B illustrates an example microbubble microscopic structure, in accordance with embodiments.

FIG. 2B illustrates an example microbubble microscopic structure 250, in accordance with embodiments. In an embodiment, the outer shell of the microbubble may comprise phospholipids 252, and the interior core 254 may be filled with fluorinated gas. In particular, microbubble structure 250 may comprise phospholipids 252 with an inter phase 254 of a fluorinated alkane, such as perfluoropropane or butane. For example, the microbubbles may comprise a synthetic phospholipid shell filled with octafluoropropane gas.

In some embodiments, the microbubble shell may be formed from block copolymers or functionalized natural polymers and fluorocarbons, and is not limited by the present disclosure. Additionally, other classes of bubbles can be formed by multiphase polymerization of styrene or similar monomers that trap a center core 254 of air.

In some embodiments, the phospholipids 252 may comprise anchoring and/or targeting moieties, such as hydrophobic tails 256, oriented toward the interior 254 of the bubble structure. Thus, structure 250 may facilitate the microbubbles' stability over long periods of time. Accordingly, unlike spontaneously-formed bubbles in a high-pressure fluid, chemically stabilized microbubble 250 may require the input of activation energy before it undergoes cavitation. The disclosed microbubbles thus act like a potential energy storage reservoir, forming stable low-pressure regions or voids 254 in the surrounding ocular fluid and/or irrigation fluid. When activation energy is provided and these voids are filled by the surrounding fluid, the fluid's motion can initiate cavitation microjets, releasing sufficient mechanical energy to fragment the cataract. Thus, chemical stabilization enables the disclosed system and methods to target a cataract preferentially, since the disclosed microbubbles can remain stable until they are deposited and activated near the cataract.

This improves over conventional techniques for cataract fragmentation because the microbubbles can more precisely target the cataract than can ultrasound waves, which are subject to dispersion, reflection, etc. Accordingly, the disclosed system and methods can significantly lower the eye's exposure to waste mechanical energy, and improve efficiency and safety of the cataract fragmentation process.

In some embodiments, microbubble 250 can have an average diameter (wherein "average diameter" refers to the largest dimension for non-spheroidal shapes) between 0.1 µm and 10 µm, or between 0.5 µm and 10 µm, or between 1 µm and 10 µm. In some embodiments, the average diameter is between 0.5 µm and 3 µm, or between 1 µm and 2 µm. In some embodiments, the microbubble 250 has an average diameter less than 10 µm, or less than 5 µm, or less than 1 µm, or less than 0.5 µm, or less than 0.1 µm. In some embodiments, microbubble 250 has an average diameter greater than 0.1 µm, or greater than 0.5 µm, or greater than 1 µm, or greater than 5 µm, or greater than 10 µm. Synthetic processes allow the production of bubbles of various sizes and materials.

The term "microbubbles" may be used interchangeably herein with "bubbles," and it will be appreciated that use of the term "microbubbles" is not intended to limit the size of the bubbles to any particular range (e.g., micron diameters).

Because the eye's lens is typically bare, the microbubbles may be able to bind to the cataractous lens without being tagged. Accordingly, in some embodiments, the microbubbles are not tagged to a lens protein in order to bind to the lens. In some embodiments, the microbubbles may be tagged and/or coated with a targeting moiety to bind to the lens protein.

After introduction of the bubbles and attachment or association of the bubbles with the target, cavitation may be initiated by a variety of methods. In some embodiments, this may involve application of activation energy, as described above. The activation energy may be generated ex vivo, for example, by the application of directed ultrasound and/or radio waves. In one example, electromagnetic (EM) energy of a frequency between 400 kHz and 10 MHz is suitable because it propagates through tissue without strong interactions (due to low electrical conductivity). In another example, standard ultrasound units are applied, either within or adjacent to the patient's body, with sufficient power to initiate cavitation of the pre-positioned bubbles. Activation of the microbubbles by applying energy is described further herein below.

FIG. 3 illustrates an example cavitation process 300, as described in "High speed observation of damage created by a collapse of a single cavitation bubble," Wear 418-419 (2019) by M. Dular et al., and in accordance with embodiments of the present disclosure. Cavitation is the process by which a microbubble 310 expands and collapses with a shock wave, causing pitting of a solid surface 315. In this example, a vapor microbubble 310 can form within a high-pressure fluid. For example, the microbubble can form spontaneously in a region of rapid flow change in the fluid. In this example, the microbubble may form spontaneously as the fluid flows around a surface, such as surface 315, especially if the surface's motion or acceleration creates large pressure gradients (e.g., in the vicinity of the phaco needle tip, propellers, or pipe areas of changing diameter). Such a surface 315 may be pitted by the cavitation process 300. Note that surface 315 may also play a role in the bubble's collapse and subsequent cavitation.

In embodiments of the present disclosure, rather than forming spontaneously, the microbubbles may be chemically stabilized (e.g., they may comprise phospholipid shells with anchoring and/or targeting moieties, such as hydrophobic tails, in the interior of the bubbles). Accordingly, the microbubbles may require activation energy to undergo cavitation, rather than cavitating spontaneously. This stabilization and activation allows the disclosed system and methods to target the cataract preferentially, thereby significantly lowering the eye's exposure to waste mechanical energy, and improving efficiency and safety of the cataract fragmentation process. As described above, such stabilized microbubbles may be formed from a precursor substance using a mixing or agitating apparatus. In some embodiments, the microbubbles may form and/or cavitate spontaneously, and are not limited by the present disclosure.

The microbubble can subsequently reach its peak or maximum size and begin to implode at a susceptible point 320 under pressure from the fluid. In this example, the region 322 (shown in projection view as the top of microbubble 320) of microbubble 320 farthest from surface 315 may collapse faster than the region 324 closest to the surface (shown as the bottom of microbubble 320). In particular, during implosion, the high-pressure fluid surrounding region 322 may accelerate into the void previously formed by the microbubble. Accordingly, the implosion can trigger a jet 330 (also referred to as a microjet) of the high-pressure fluid, which can divide and annihilate the microbubble. The jet 330 may reach very high speeds, such as hundreds of meters per second.

Moreover, the jet can deform 340 nearby surface 315. In embodiments of the present disclosure, the surface 315 can be the cataractous lens. The microbubbles can be designed to preferentially damage stiff surfaces, such as the cataract, while preserving pliable tissue, such as the lens capsule. Upon collision with the surface 315, jet 330 can be deflected 350 along surface 315, possibly forming eddies 355. Such eddies 355 can form secondary microbubbles 360, which may be smaller than the original bubble. Due to their very small size, secondary microbubbles 360 may have sufficient surface tension to remain spherical while imploding, thereby producing shock waves 370 which can further damage surface 315.

In embodiments of the present disclosure, directed cavitation enables the selective fragmentation of objects in vivo while preserving adjacent tissues. The cavitation effect is related to the stiffness of the material. In embodiments of the present disclosure, the cataract can have a higher stiffness than the surrounding tissue of the lens capsule. Therefore, it can be damaged and destroyed by cavitation, while the lens capsule and surrounding tissues are preserved. This selectivity can be further augmented by tagging the surface of the microbubbles with a targeting moiety or reagent that specifically binds to the phakic lens. Such tags can include polypeptides or acidic groups.

Figure 4:
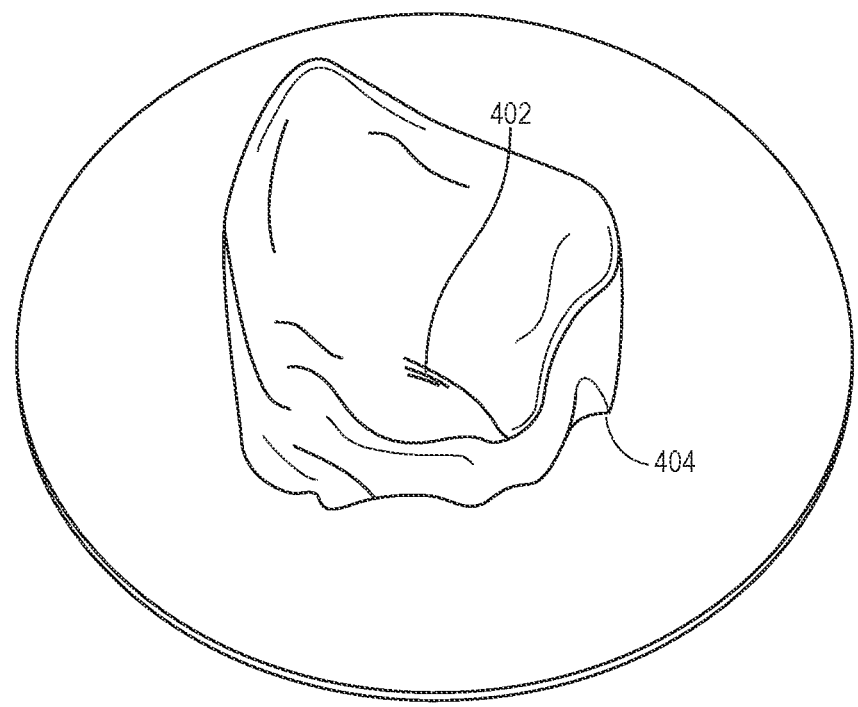
FIG. 4 illustrates intended damage to a sample by successive cycles of microbubble cavitation, in accordance with an embodiment.
Figure 5:
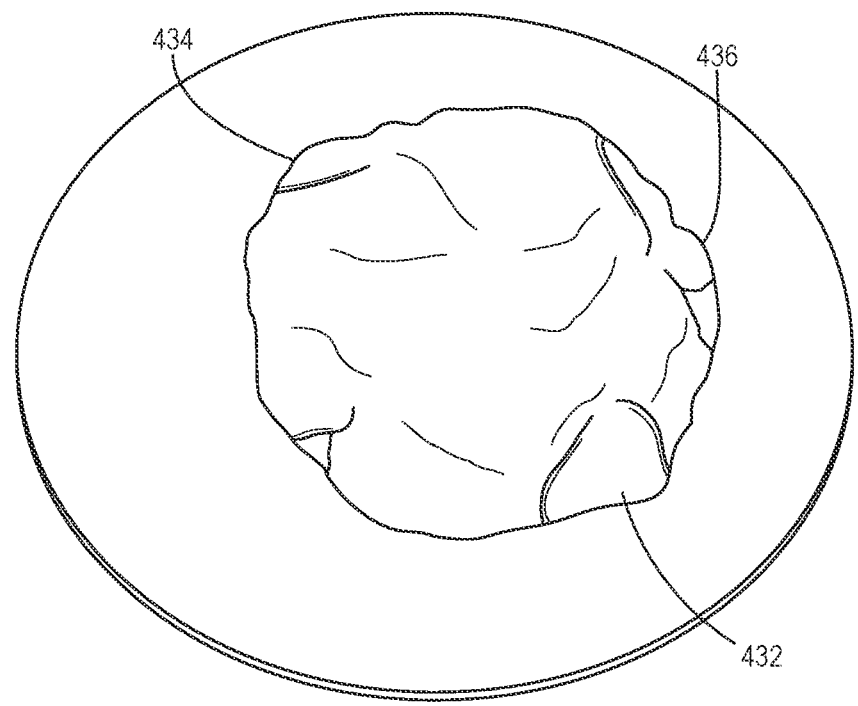
FIG. 5 illustrates successive damage to the sample of FIG. 4.
Figure 6:
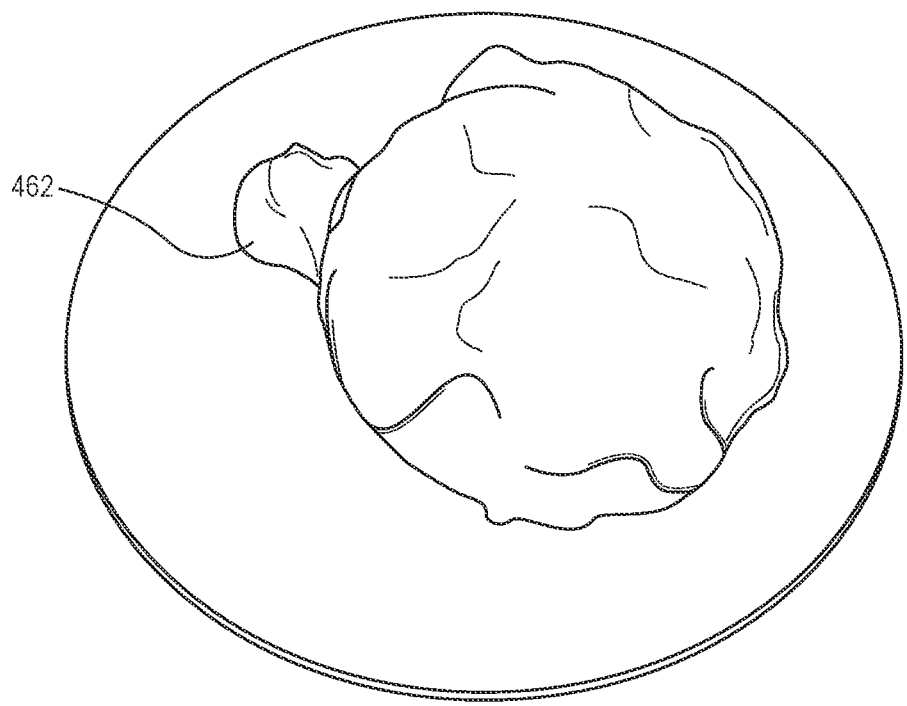
FIG. 6 illustrates successive damage to the sample of FIG. 4.

FIGS. 4-6 illustrate damage to a sample by successive cycles of microbubble cavitation. In some embodiments, multiple cycles of microbubble cavitation may be performed during the course of the cataract removal surgery. A respective cycle may include injecting or otherwise inserting bubbles to a small area inside the lens capsule, applying ultrasound energy, assessing damage to the lens, and optionally vacuuming, aspirating, or removing debris. In the example of FIG. 4, after a first cavitation cycle, the sample remains largely intact, but shows some chipping 402 and 404, and loss of mass. In FIG. 5, subsequent to a second cavitation cycle, the sample is significantly notched 432, rounded at edges 434 and 436, and scuffed, with jagged edges. In FIG. 6, subsequent to another cavitation cycle, the sample has fractured, with a broken chip 462 visible.

Figure 7:
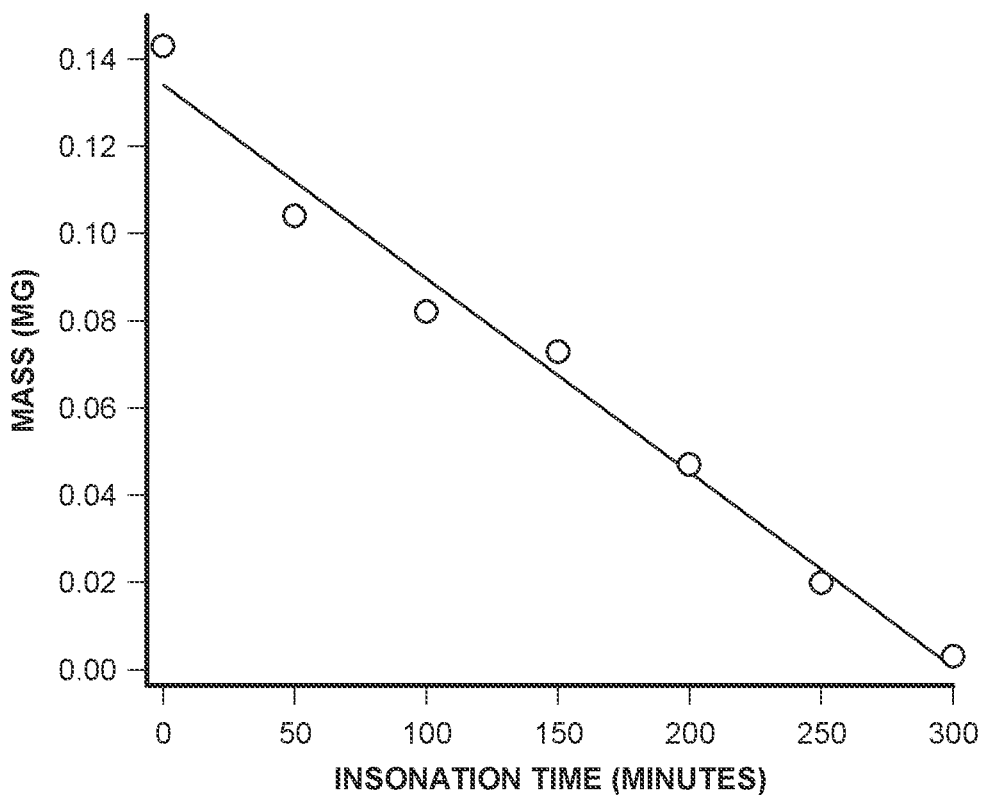
FIG. 7 is a chart showing measured damage to a sample's mass vs. ultrasound exposure time, in accordance with an embodiment.

FIG. 7 is a chart illustrating measured damage to a sample's mass vs. ultrasound exposure time, in accordance with an embodiment. In this example, the sample has an initial mass of approximately 143 µg. With subsequent ultrasound insonation of cavitating microbubbles, its mass is reduced linearly with time. Note that, in this example, after sufficient insonation time, the sample can be reduced to nearly zero mass. Accordingly, the results shown in FIG. 7 demonstrate that the disclosed cavitation process is effective and can fully and completely fragment a cataract.

III. Cataract Removal Via Cavitating Microbubbles

The disclosed system and methods can use cavitating microbubbles, such as those in the examples of FIGS. 2A and 2B above, to fragment and extract cataracts more expediently, efficiently, and safely than conventional phacoemulsification. In some embodiments, the disclosed system for cataract fragmentation has two primary components: first, microbubbles formed by the techniques described above; and second, an ultrasonic transducer. As demonstrated in the examples of FIGS. 4-7, the cavitating microbubbles can efficiently and fully fragment the cataract, without damaging the lens capsule.

In accordance with embodiments of the present disclosure, the microbubbles may first be injected into or around the cataractous lens intraoperatively. In particular, the microbubbles may either be admixed into the irrigating solution (as described, for example, in FIG. 11A below), or be injected directly (i.e., in a separate syringe) into the eye. These microbubbles can either be tagged to a lens protein or untagged.

Next, the microbubbles can be stimulated via ultrasound to induce cavitation, either from a probe external to the eye or ab interno, from an instrument inserted into the eye. In some embodiments, the ultrasound probe may be a relatively small external wand. In some embodiments, electromagnetic (EM) energy, such as radio waves of frequencies between 400 kHz and 10 MHz may be used to stimulate the microbubbles to induce cavitation, and is not limited by the present disclosure. In particular, such EM energy can propagate through tissue without strong interactions (due to low electrical conductivity). In some embodiments, other frequencies of radiation may be used, e.g. radio waves of frequencies greater than 10 MHz, and are not limited by the present disclosure.

Subsequently, the microbubbles in and around the lens can cavitate (i.e., undergo cavitation) in response to ultrasonic stimulation, and the resultant microjets can preferentially fragment the lens. This cavitation can fragment the cataractous lens, minimizing or eliminating the need for high-energy phacoemulsification. In particular, by minimizing phacoemulsification energy, use of microbubbles reduces such complications as: rupture of the thin protective posterior capsule, vitreous loss, damage to the endothelial cells, corneal edema, delayed healing, and corneal decompensation. Finally, the fragmented lens can be aspirated, and this process can be repeated in multiple cycles until the cataract is fully removed (as illustrated in the examples of FIGS. 4-6 above).

In some embodiments, the procedure may be preceded by making a small opening in the anterior surface of capsular bag (capsulorhexis), and may further include irrigation of fluid around the lens to mobilize it (hydrodissection), and removing the cataract from the eye. Subsequently, an artificial lens can be inserted into the lens capsule.

Figure 8:
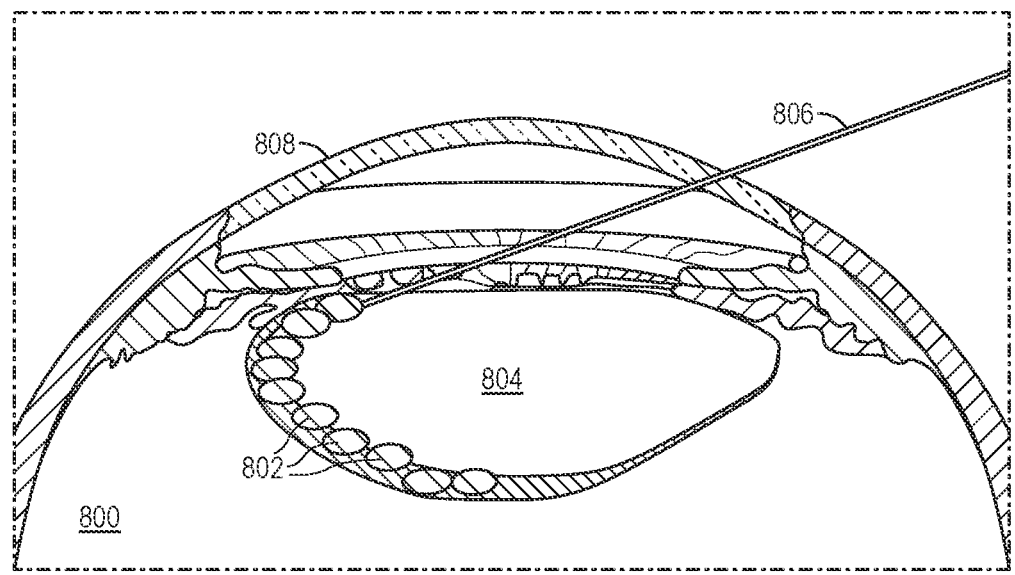
FIG. 8 illustrates injection of microbubbles about a cataract, in accordance with external activation embodiments of the present disclosure.

FIG. 8 illustrates injection of microbubbles 802 about a cataract 804, in accordance with external activation embodiments of the present disclosure. In this example, after capsulorhexis and hydrodissection of the lens, the surgeon may inject microbubbles 802, such as the microbubbles of FIGS. 2A and 2B, in and/or around the cataractous intraocular lens 804. In this example, microbubbles 802 are injected directly using syringe 806 into the eye 800. In some embodiments, the microbubbles may instead be admixed into the irrigating solution. In this example, microbubbles 802 are arranged around cataract 804 and in proximity to it. An ultrasonic probe (not shown) may also be positioned externally to the eye, by contrast with the surgically inserted phacoemulsification probe of conventional methods, so as to activate cavitation of the microbubbles.

Note that injection of the microbubbles 802 does not require as large an incision in the cornea 808 as would normally be required in conventional phacoemulsification.

In this example, injection of a thin needle tip 806 suffices to position microbubbles 802 precisely, prior to cavitation. Moreover, the other surgical instruments, such as aspiration and/or irrigation instruments, also do not require large incisions. Thus, in embodiments where the microbubbles are admixed in the irrigating solution, the incision can still be significantly smaller than in phacoemulsification. Such a smaller incision may improve the safety, healing time, and stability of the disclosed method, as well as enabling a broader choice of artificial lens, and broader choices of other aspects of the surgery.

In external activation embodiments, cavitation of the microbubbles 802, activated by directed ultrasound energy as described herein below, may be the primary source of mechanical energy used to fragment cataract 804. Thus, in external activation embodiments, the ultrasound acts essentially as a trigger that activates the cavitation, rather than directly fragmenting the cataract. In some embodiments, a surgical 'chopper' instrument, and/or conventional phacoemulsification ultrasound energy, may also be used to augment the fragmentation.

Figure 9:
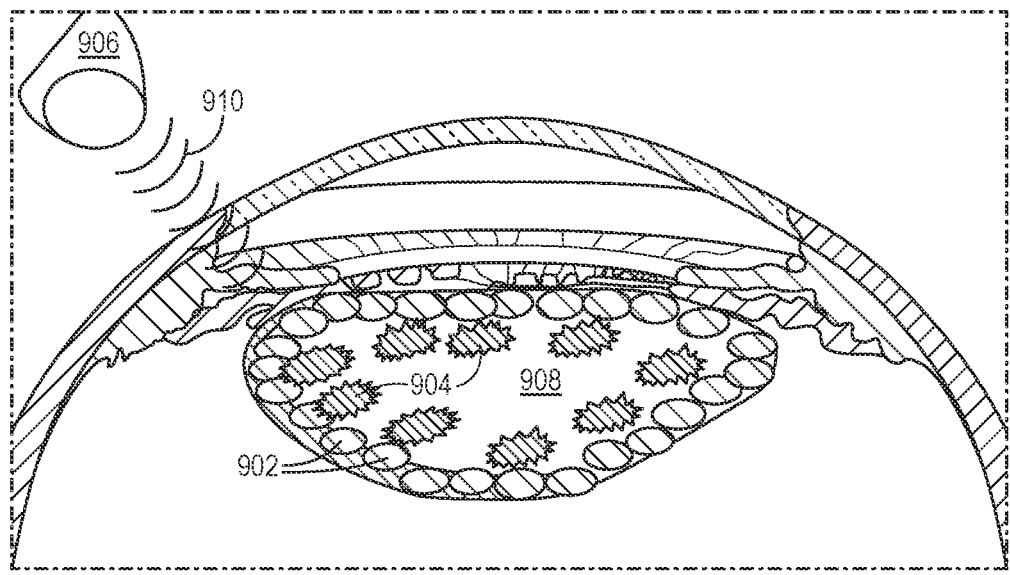
FIG. 9 illustrates activation of microbubbles to cavitate, in accordance with external activation embodiments of the present disclosure.

FIG. 9 illustrates activation of microbubbles 902 to cavitate 904, in accordance with external activation embodiments of the present disclosure. In this example, low energy ultrasound may be directed from the ultrasonic probe 906 to the microbubbles 902 surrounding the crystalline lens 908. The microbubbles 902 can be activated by the ultrasound energy 910, thereby inducing them to undergo cavitation 904.

In this example, the cavitation 904, rather than the direct action of the ultrasound, fragments the cataractous lens 908. The ultrasound energy 910 may be lower-power, less sharp, and/or more directional than in conventional phacoemulsification, thereby being safer to surrounding tissue and targeting the microbubbles 902 far more precisely than conventionally. In conventional phacoemulsification methods, by contrast, a higher level of ultrasound energy is propagated much more broadly throughout the surgical region, so as to fragment the cataract by its direct action. Accordingly, the disclosed system and methods can use lower energy and provoke fewer complications than conventional phacoemulsification.

The injection and/or cavitation of microbubbles can be repeated in multiple cycles, as necessary, in order to fragment the lens thoroughly. Such fragmentation allows for aspiration of the emulsified cataract using standard irrigation/aspiration instrumentation. As described in the examples of FIGS. 4-6 above, each cycle can significantly damage the cataract, leading eventually to complete extraction and removal. In particular, cycles may include injecting bubbles to a small area inside the lens capsule, applying ultrasound energy, assessing damage to the lens, and optionally vacuuming or removing debris. Such cycles are described further in the example flow of FIG. 13 below.

Figure 10:
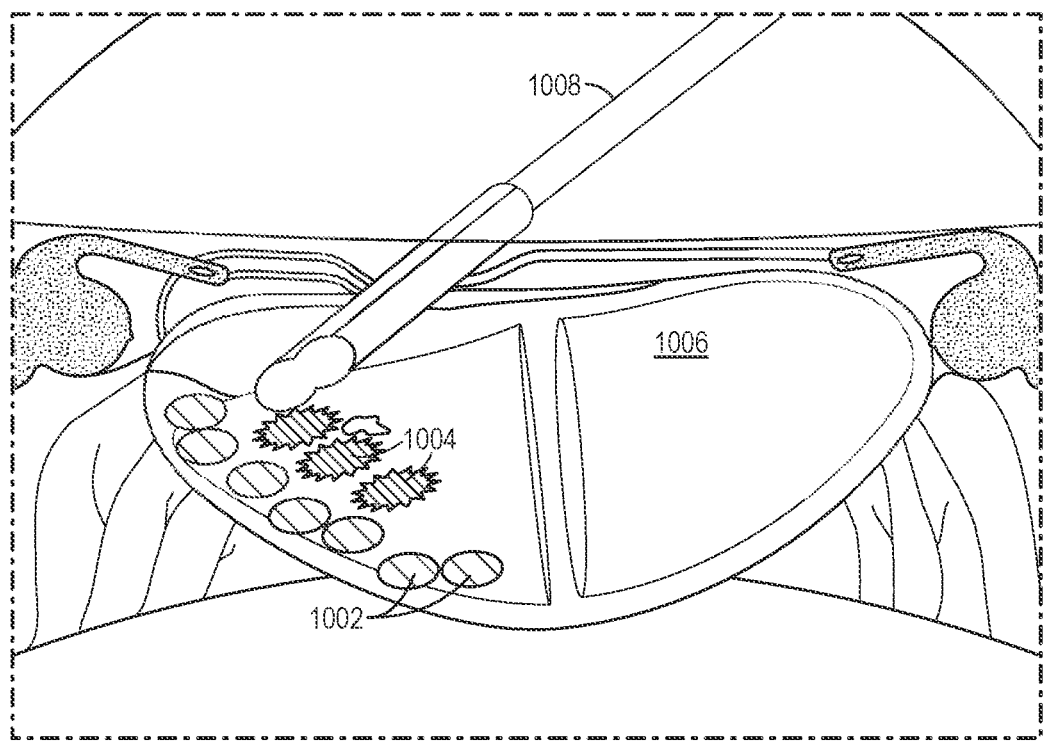
FIG. 10 illustrates activation of microbubbles to cavitate, in accordance with internal activation embodiments of the present disclosure.

FIG. 10 illustrates activation of microbubbles 1002 to cavitate 1004, in accordance with internal activation embodiments of the present disclosure. In this example, after capsulorhexis and hydrodissection of the cataractous lens 1006, an internal microbubble activation instrument 1008 may be introduced, which combines the functions of irrigation and aspiration with those of an ultrasonic probe. By contrast with a conventional phacoemulsification handpiece, microbubble activation instrument 1008 would not require a sharp tip, making it safer. Moreover, microbubble activation instrument 1008 may be smaller than a conventional phacoemulsification handpiece, and therefore may be inserted using a significantly smaller corneal incision than the phacoemulsification handpiece, as in the example of FIG. 9 above. The instrument 1008 may irrigate the lens with a microbubble solution. Instrument 1008 may also emit ultrasonic waves from its tip to activate microbubbles in its proximity, triggering focal cavitation and lens fragmentation. The instrument may then perform aspiration to remove the ensuing lens fragments. In an embodiment, a so-called IA (Irrigation and Aspiration) tip may be used.

As in the external activation embodiments described above, cavitation of the microbubbles 1002 and 1004, activated by directed ultrasound energy emitted from instrument 1008, may also be the primary source of mechanical energy used to fragment cataract 1006 in internal activation embodiments. Thus, in internal activation embodiments, the ultrasound energy from instrument 1008 acts to activate or trigger cavitation, rather than directly fragmenting cataract 1006. Accordingly, the ultrasound can be low in energy and can be directed so as to target microbubbles 1002 and 1004 precisely, rather than being aimed broadly at cataract 1006. In some embodiments, a surgical 'chopper' instrument may also be used to augment the cavitation.

Thus, instrument 1008 may be used in a similar manner to a conventional phacoemulsification handpiece, but instrument 1008 does not require a sharp tip, making the risk of complication far lower. In addition, as in the external activation embodiments described above, the ultrasound energy emitted by microbubble activation instrument 1008 may be significantly lower in energy and more precisely directed than in conventional phacoemulsification, lowering the risk of burns. The instrument 1008 can also be smaller and less sharp than a phacoemulsification handpiece, allowing for a smaller corneal incision, and can be less sharp. Moreover, combining the irrigation and aspiration functions with the ultrasound probe simplifies the procedure and reduces the number of instruments that must be inserted in the eye, potentially further lowering the complication risk.

Figure 11A:
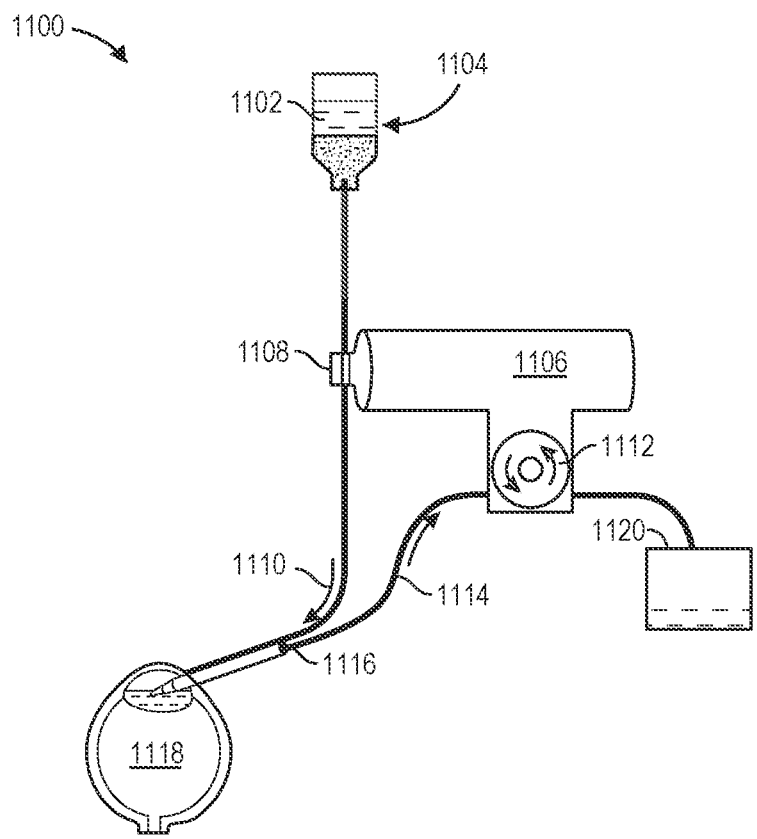
FIG. 11A illustrates an example surgical system, in accordance with phaco-augmentation embodiments of the present disclosure.

FIG. 11A illustrates an example surgical system 1100, in accordance with phaco-augmentation embodiments of the present disclosure. Phaco-augmentation embodiments can make use of standard phacoemulsification systems and methods, augmented by the cavitation action of the activated microbubbles 1102 to fragment a cataractous lens. Thus, in phaco-augmentation embodiments, surgical system 1100 can be similar to a standard phacoemulsification system, but unlike a conventional system, system 1100 can include microbubbles 1102.

In particular, in this example, microbubbles 1102 may be admixed into the irrigating fluid in irrigation bottle 1104, which can comprise a balanced salt solution, as in a standard phacoemulsification system. Irrigation bottle 1104 may be of adjustable height in order to regulate the fluid pressure by gravity fluidics. Phaco machine 1106 may include pinch valve 1108, which controls inflow 1110 of the irrigation fluid, and pump 1112, which regulates outflow 1114 of aspirated fluid from the phaco handpiece 1116 during cataract removal surgery on eye 1118. Thus, inflow 1110 of the irrigation fluid may transport microbubbles 1102 to the cataract within eye 1118 in a comparatively non-invasive manner. In some embodiments, the microbubbles may instead be injected directly via a syringe.

When pinch valve 1108 is open, the fluid in irrigation bottle 1104 can produce pressure in the anterior chamber of eye 1118. During surgery, the aspirated fluid containing the emulsified cataract can be pumped 1114 from eye 1118 by pump 1112. The height of irrigation bottle 1104 may be set to match the inflow 1110 of irrigation fluid to the outflow 1114 of aspirated fluid. Pump 1112 can include a flow pump, such as a peristaltic pump, and/or a vacuum pump, such as a venture pump. Phaco machine 1106 may filter waste, such as the emulsified cataract, from the aspirated fluid into waste bag 1120.

Figure 11B:
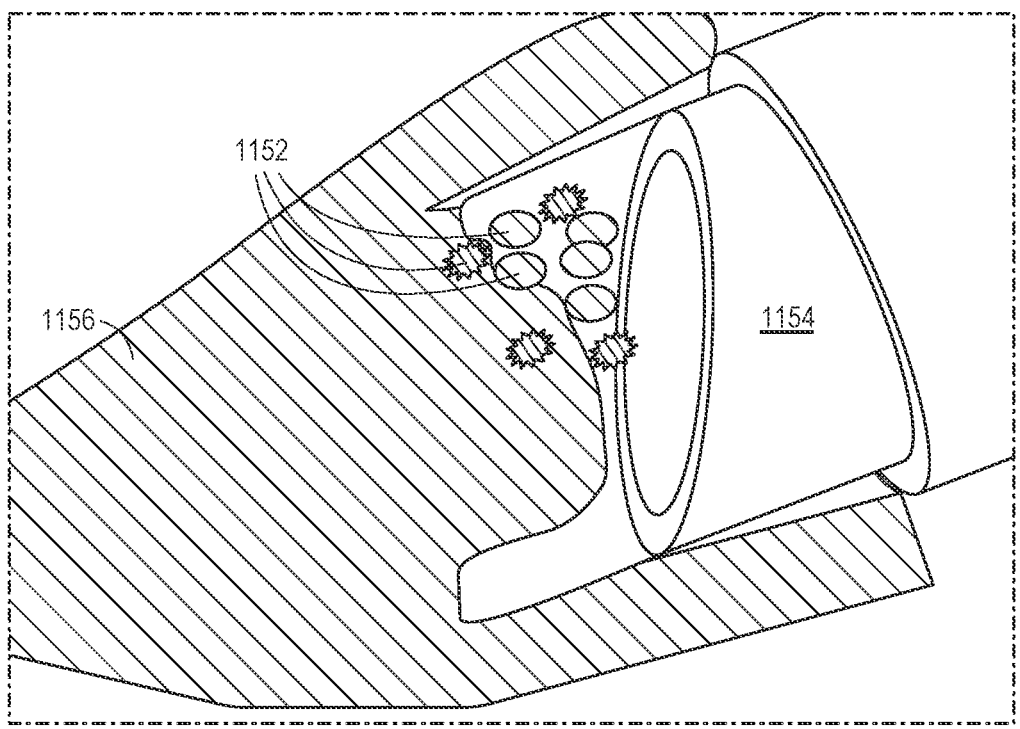
FIG. 11B is an inset view of activation of microbubbles to cavitate by a surgical system phaco tip of FIG. 11A.

FIG. 11B is an inset view of activation of microbubbles 1152 to cavitate by a surgical system phaco tip 1154 of FIG. 11A, in accordance with phaco-augmentation embodiments of the present disclosure. In this example, after capsulorhexis and hydrodissection of the cataractous lens 1156, the cataract 1156 may be irrigated with microbubbles 1152. As described in the example of FIG. 11A above, the irrigation fluid used to replace the hydrodissected cataract may contain microbubbles 1152, which can be deposited on and around cataract 1156.

In phaco-augmentation embodiments, a standard phacoemulsification handpiece 1154 may be used to fragment the lens 1156 with mechanical ultrasound energy, augmented by the cavitation action of the activated microbubbles 1152. In particular, the ultrasound energy from phaco handpiece 1154 can activate microbubbles 1152, which can cavitate and help to fragment cataract 1156.

By combining the fragmentation power of phacoemulsification and microbubble cavitation, the disclosed system and methods may require far less phacoemulsification energy compared to conventional phacoemulsification. Consequently, the procedure may cause fewer complications.

Figure 12:
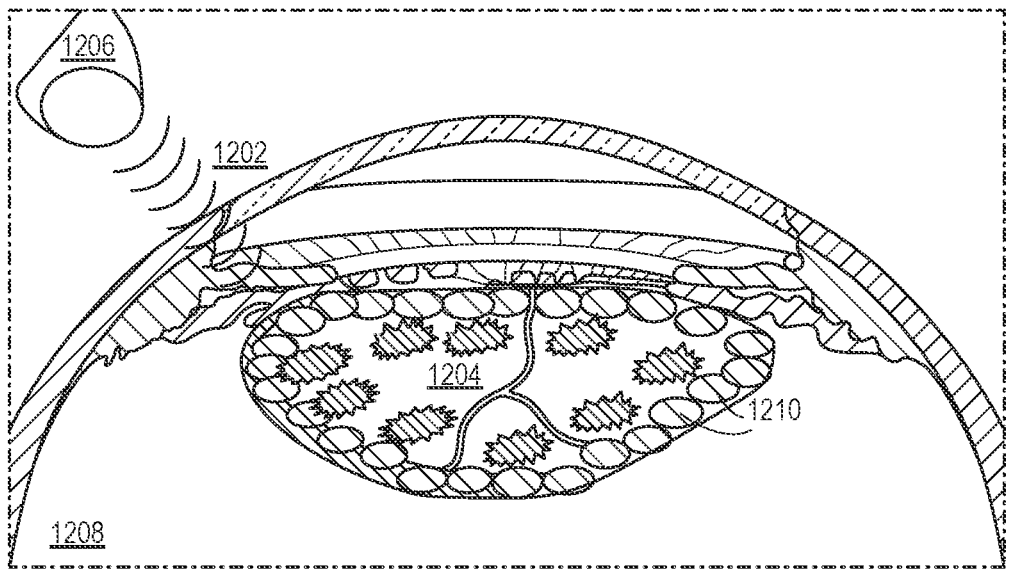
FIG. 12 illustrates directionality of the ultrasound waves and precision of the targeted damage to the cataract, in accordance with embodiments of the present disclosure.

FIG. 12 illustrates directionality of the ultrasound waves 1202 and precision of the targeted damage to the cataract 1204, in accordance with embodiments of the present disclosure. As described above, the disclosed system and methods can improve significantly over conventional phacoemulsification techniques for cataract removal. In particular, the disclosed system and methods can improve safety and efficiency of cataract removal surgery, reduce costs associated with phacoemulsification, and lower training requirements for ophthalmological surgical residents. Whereas phacoemulsification surgical training is currently a key component of the 3-year ophthalmic surgery residency, in some embodiments, the disclosed procedures for cataract fragmentation based on microbubble cavitation could be taught to surgeons in much less time.

As described in the example of FIG. 1B above, the complication of capsular bag rupture can happen easily, and is relatively common in phacoemulsification procedures. Accordingly, preventing capsular bag rupture is one of the principal components of the training requirements. By contrast, particularly in internal and external activation embodiments, the disclosed system and methods does not require relatively sharp instruments. As described in the example of FIG. 10, even the internal microbubble activation instrument 1008 does not require a sharp tip. Likewise, in external activation embodiments, as in the example of FIG. 12, the ultrasonic probe 1206 can be completely external to the eye 1208. Accordingly, the risks of capsular bag rupture and/or damage to other structures in the eye, such as the cornea or iris, may be far lower using the disclosed system and methods, than with conventional phacoemulsification. Moreover, microbubbles 1210 may preferentially damage stiff surfaces, such as cataract 1204, while preserving pliable tissue, such as the capsular bag. In this example, cataract 1204 is fragmented into multiple pieces, while the capsular bag remains intact.

In addition, as described above, the disclosed system and methods are particularly advantageous because less ultrasound and/or mechanical energy may be needed than in conventional phacoemulsification. This is true both because a smaller amount of energy is required to activate the microbubbles to cavitate (rather than directly fragmenting the cataract), and because the microbubbles themselves can more precisely target the cataract than can propagating ultrasound waves, which are subject to dispersion, reflection, etc. Accordingly, the eye is exposed to significantly less waste mechanical energy than in conventional methods, thereby improving efficiency and safety of the fragmentation process.

In particular, there is less danger of burns than in conventional phacoemulsification because less ultrasound energy 1202 is used, and because the ultrasonic probe 1206 can be external to eye 1210. Moreover, the lower ultrasound dose than in conventional phacoemulsification can also reduce the risk of damage to corneal endothelial cells and other ocular structures and tissues.

In addition, the disclosed system and methods require much smaller incision than conventional phacoemulsification, at least in the internal and external activation embodiments. Such a smaller incision may improve the stability of the disclosed method, as well as enabling a broader choice of artificial lens.

IV. Method for Cataract Removal with Cavitating Microbubbles

Figure 13:
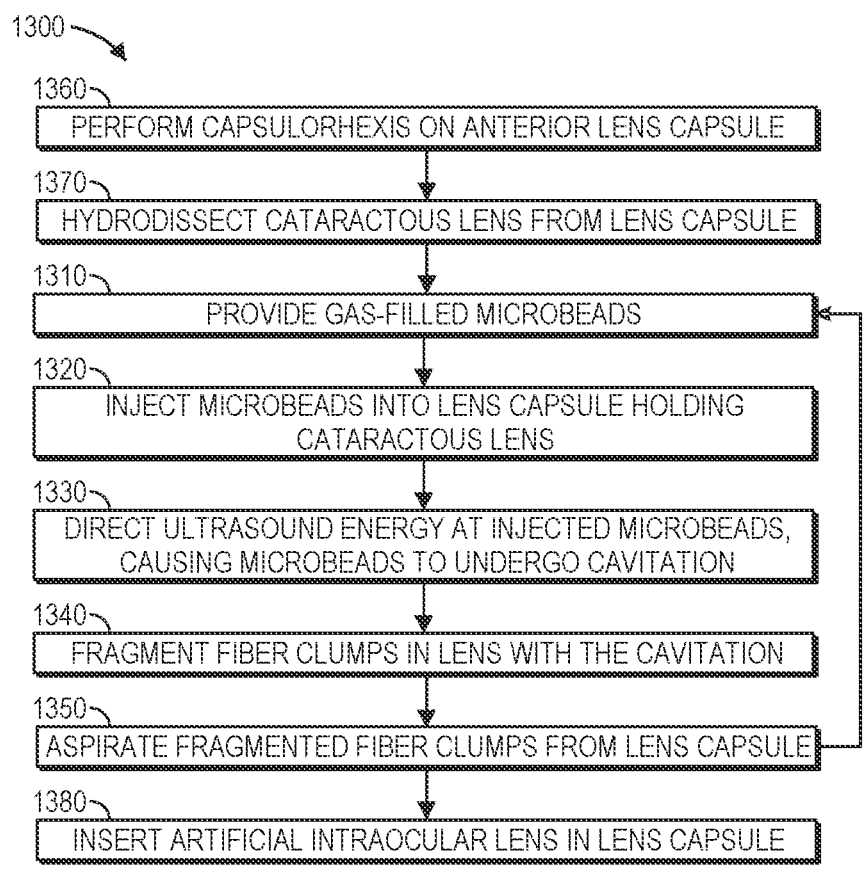
FIG. 13 is a flowchart illustrating a process for cataract fragmentation and extraction via microbubble cavitation, in accordance with embodiments of the present disclosure.

FIG. 13 is a flowchart illustrating process 1300 for cataract fragmentation and extraction via microbubble cavitation, in accordance with embodiments of the present disclosure.

Optionally, in operation 1360, a capsulorhexis is performed on the anterior lens capsule.

Optionally, in operation 1370, the cataractous lens is hydrodissected from the lens capsule. In some embodiments, the microbeads are injected with hydrodissecting liquid (in combination with operation 1320 below).

In operation 1310, gas-filled microbeads are provided. The gas-filled microbeads can have an outside diameter less than 500 microns. In some embodiments, the outside diameter may be less than 250 microns or less than 100 microns. In some embodiments, each of the microbeads is comprised of a phospholipid shell and a fluorinated alkane gas inside the shell. In some embodiments, the fluorinated alkane gas is selected from the group consisting of perfluoropropane and butane. In some embodiments, each of the microbeads is comprised of a multiphase polymer shell and air inside the shell. In some embodiments, the microbeads are coated with a targeting moiety configured to bind to lens material (e.g., lens fiber protein or another lens material). The method may further comprise binding the microbeads to lens material of the cataractous lens. In some embodiments, the targeting moiety comprises polypeptides or acidic groups.

In operation 1320, the microbeads are injected into a lens capsule that holds a cataractous lens of a subject. In some embodiments, the microbeads are in a liquid suspension, and the injecting includes injecting the liquid suspension into the lens capsule. In some embodiments, the liquid suspension is hydrodissecting liquid and/or is used to irrigate the lens capsule. In some embodiments, the subject is human. In others, the subject can be an animal, such as a dog, rabbit, or pig.

In operation 1330, ultrasound energy is directed at the injected microbeads sufficient to cause the microbeads to undergo cavitation. In some embodiments, the ultrasound energy reaches the microbeads by being transmitted through biological tissue from outside of the lens capsule. In some embodiments, the ultrasound energy is transmitted from within the lens capsule using an ultrasonic tip.

In operation 1340, lens material are fragmented in the lens with the cavitation while preserving the posterior lens capsule.

In operation 1350, the fragmented lens clumps are aspirated from the lens capsule.

The injection and/or cavitation of microbubbles can be repeated in multiple cycles, as necessary, in order to fragment the lens thoroughly. Optionally, following operation 1350, process 1300 may return to operation 1310, and additional cycles of microbubble cavitation may be performed. Such cycles may repeat operations 1310 through 1350, as needed to fragment the cataractous lens. In particular, cycles may include injecting bubbles to a small area inside the lens capsule, applying ultrasound energy, assessing damage to the lens, and optionally vacuuming or removing debris. As described in the examples of FIGS. 4-6 above, each cycle can significantly damage the cataract, leading eventually to complete extraction and removal.

Optionally, following operation 1350 and/or any additional cycles, in operation 1380, an artificial intraocular lens is inserted into the lens capsule.

In some embodiments, the method further comprises inserting a phacoemulsification handpiece tip into the lens capsule. The method may further comprise emulsifying, during or after the fragmenting, the lens clumps using emulsifying ultrasonic energy transmitted from the phacoemulsification handpiece tip within the lens capsule. Less emulsifying ultrasonic energy from the phacoemulsification handpiece tip inside the lens capsule may be required to remove the cataractous lens than if the fragmenting with the cavitation were not performed.

The invention has been described with reference to various specific and illustrative embodiments. However, it should be understood that many variations and modifications may be made while remaining within the spirit and scope of the following claims.

What is claimed is:

1. A method for removing a lens from an eye, the method comprising:
   injecting microbeads into the eye of a subject;
   directing energy at the injected microbeads sufficient to cause the microbeads to undergo cavitation;
   fragmenting lens material of the eye with the cavitation; and
   aspirating the fragmented lens material from the eye.

2. The method of claim 1 further comprising:
   repeating the injecting, directing, fragmenting, and aspirating to remove the entire lens from the subject.

3. The method of claim 1 wherein each of the microbeads is comprised of:
   a phospholipid shell; and
   a fluorinated alkane gas inside the phospholipid shell.

4. The method of claim 3 wherein the fluorinated alkane gas is selected from the group consisting of perfluoropropane and butane.

5. The method of claim 1 wherein each of the microbeads is comprised of:
   a block copolymer or functionalized natural polymer shell; and
   a fluorocarbon gas inside the shell.

6. The method of claim 1 wherein each of the microbeads is comprised of:
   a multiphase polymer shell; and
   air inside the shell.

7. The method of claim 1 wherein the microbeads are coated with a targeting moiety configured to bind to the lens material, the method further comprising:
   binding the microbeads to the lens material of the lens.

8. The method of claim 7 wherein the targeting moiety comprises polypeptides or acidic groups.

9. The method of claim 1 further comprising:
   performing a capsulorhexis on the eye;
   hydrodissecting the lens from the eye; and
   inserting an artificial intraocular lens into the eye.

10. The method of claim 9 wherein the injecting of the microbeads is performed with hydrodissecting liquid.

11. The method of claim 1 wherein the microbeads are in a liquid suspension, and the injecting includes injecting the liquid suspension into the eye.

12. The method of claim 11 wherein the liquid suspension is used to irrigate the eye.

13. The method of claim 1 wherein the microbeads are injected into or around the lens.

14. The method of claim 1 wherein the energy reaches the microbeads by being transmitted through biological tissue from outside of the eye.

15. The method of claim 1 wherein the energy is transmitted from within the eye using an ultrasonic tip.

16. The method of claim 1 further comprising:
   inserting a phacoemulsification handpiece tip into the eye; and
   emulsifying, during or after the fragmenting, the lens material using emulsifying energy transmitted from the phacoemulsification handpiece tip within the eye,
   wherein less emulsifying energy from the phacoemulsification handpiece tip inside the eye is required to remove the lens than if the fragmenting with the cavitation were not performed.

17. The method of claim 1 wherein the subject is one or more of:
   a human;
   a dog; or
   a rabbit.

18. The method of claim 1 wherein the microbeads are injected into a lens capsule of the eye.

19. A system for removing a lens from an eye of a subject, the system comprising:
   stabilized gas-filled microbeads having an outside diameter less than 500 microns, wherein the stabilized gas-filled microbeads are suitable for injecting into the eye and configured to undergo cavitation when subjected to ultrasound energy;
   a microbubble activation instrument configured to direct ultrasound energy to the injected stabilized gas-filled microbeads sufficient to cause the microbeads to undergo cavitation and fragment lens material with the cavitation while preserving a lens capsule of the eye.

20. The system of claim 19 wherein the microbubble activation instrument includes:
   an ultrasonic tip for transmitting the ultrasound energy from within the eye; or
   a phacoemulsification handpiece tip for inserting into the eye.

* * * * *